United States Patent [19]

Liu et al.

[11] Patent Number: 5,029,482
[45] Date of Patent: Jul. 9, 1991

[54] GAS/LIQUID FLOW MEASUREMENT USING CORIOLIS-BASED FLOW METERS

[75] Inventors: Ke-Tien Liu, Cerritos; Tanh V. Nguyen, Fullerton, both of Calif.

[73] Assignee: Chevron Research Company, San Francisco, Calif.

[21] Appl. No.: 414,034

[22] Filed: Sep. 28, 1989

Related U.S. Application Data

[63] Continuation-in-part of Ser. No. 307,156, Feb. 3, 1989, abandoned, which is a continuation of Ser. No. 112,350, Oct. 22, 1987, abandoned.

[51] Int. Cl.$^5$ .............................................. G01F 1/74
[52] U.S. Cl. ............................ 73/861.04; 73/61.00 R; 73/61.10 R; 73/831.38
[58] Field of Search ............. 73/861.04, 861.38, 61 R, 73/61.1 R

[56] References Cited

U.S. PATENT DOCUMENTS

| | | | |
|---|---|---|---|
| 4,662,219 | 5/1987 | Nguyen | 73/861.04 |
| 4,689,989 | 9/1987 | Aslesen et al. | 73/861.04 |
| 4,773,257 | 9/1988 | Aslesen et al. | 73/61.1 R |
| 4,823,613 | 4/1989 | Cage et al. | 73/861.38 |
| 4,872,351 | 10/1989 | Ruesch | 73/861.04 |

*Primary Examiner*—Hezron E. Williams
*Assistant Examiner*—Craig Miller
*Attorney, Agent, or Firm*—Edward J. Keeling; David J. Power; Robert D. Touslee

[57] ABSTRACT

A method of determining mass flow rate and phase distribution of gas/liquid two-phase flows is disclosed. The method uses a Coriolis-based mass flow meter. Flow streams of known mass flow rate and phase distribution are directed through the meter and correlation factors are obtained using an apparent mass flow rate output and an apparent density output from the Coriolis meter. The true mass flow rate and phase distribution of unknown flow streams can then be determined.

7 Claims, 2 Drawing Sheets

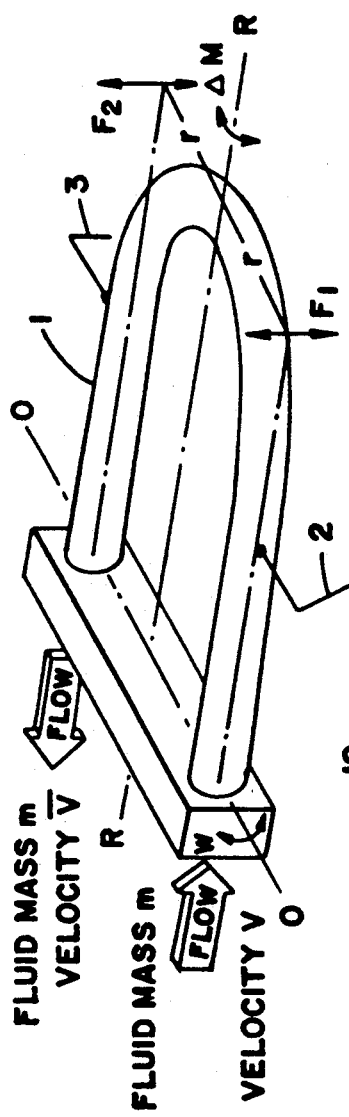
FIG_1
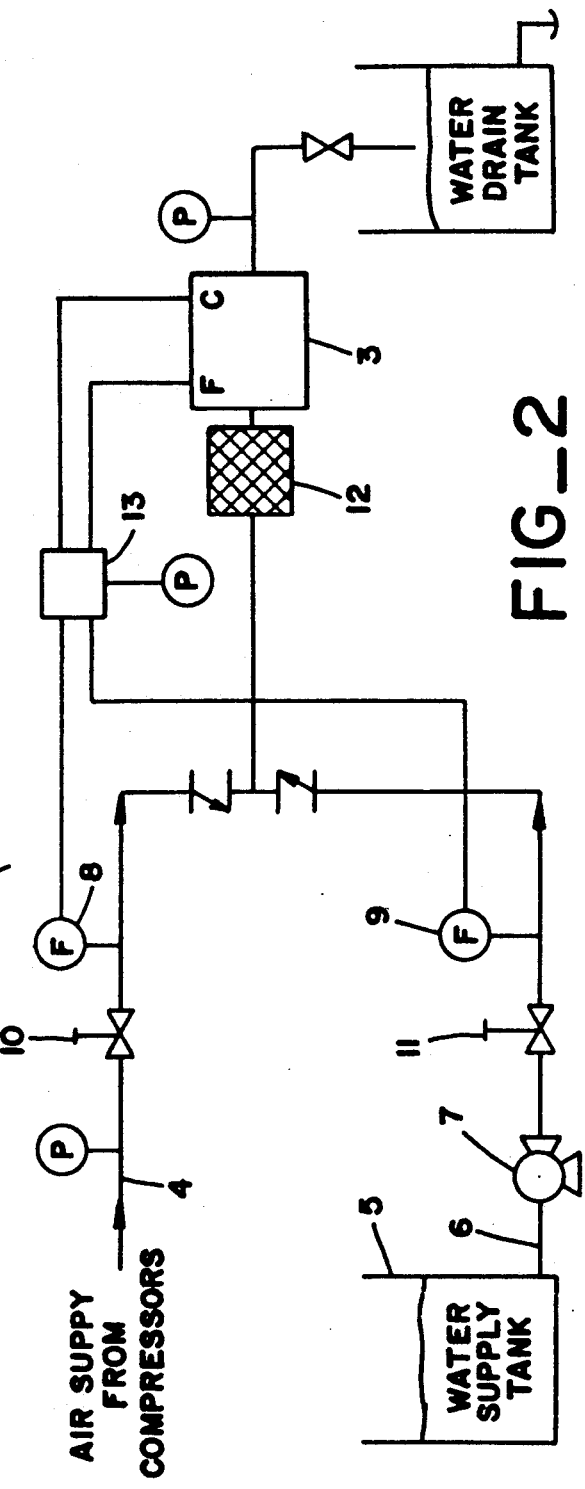
FIG_2

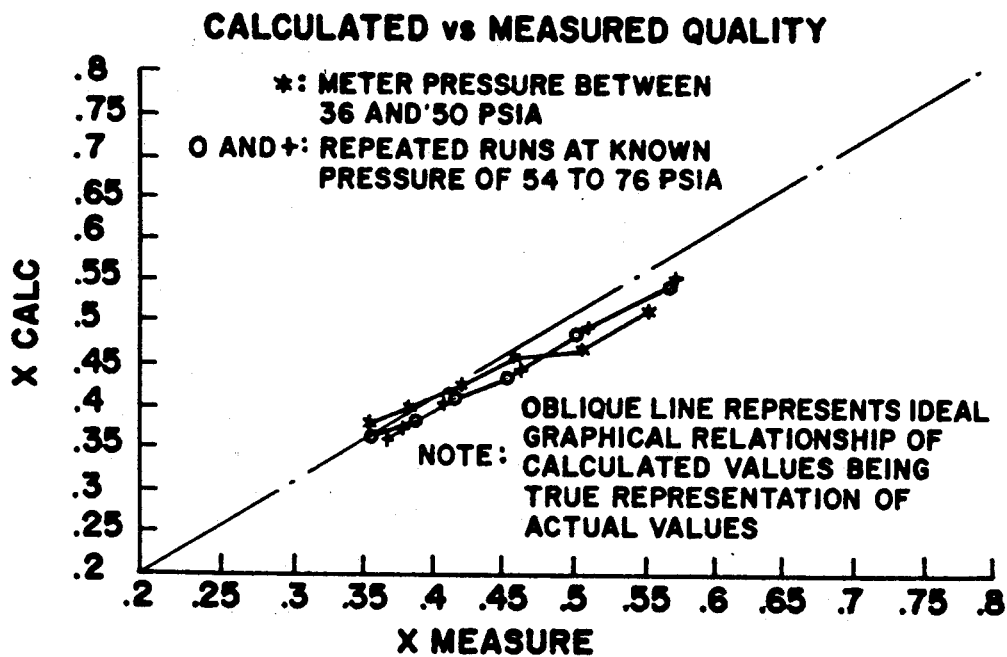
FIG_3
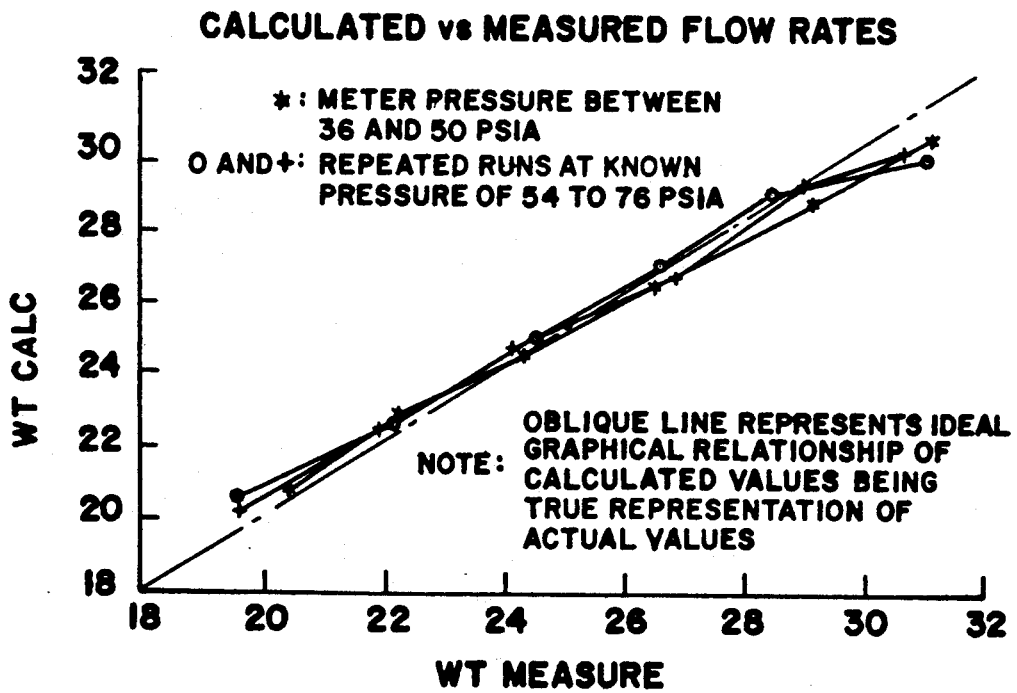
FIG_4

GAS/LIQUID FLOW MEASUREMENT USING CORIOLIS-BASED FLOW METERS

CROSS REFERENCE TO RELATED APPLICATIONS

This is a continuation-in-part of U.S. application Ser. No. 307,156, filed Feb. 3, 1989, which is a continuation of U.S. application Ser. No. 112,350, filed Oct. 22, 1987, now abandoned.

BACKGROUND OF THE INVENTION

The present invention relates to the field of two-phase flow measurement. In particular, the present invention provides a method and apparatus for measuring the relative quantities of gas and liquid in a flowing fluid stream, especially for the measurement of wet steam.

One method of enhancing recovery of hydrocarbons in, for example, oil-bearing reservoirs, is to inject steam. In order to properly manage this enhanced recovery technique, it is necessary to know the "quality" and the mass flow rate of steam that is injected, wherein the "quality" is defined as the ratio of vapor to vapor plus liquid of the injected steam.

Many methods have been proposed for the measurement of steam quality in surface steam lines. For example, U.S. Pat. No. 4,662,219, to Nguyen, incorporated by reference herein for all purposes and assigned to the assignee of the present invention, discloses a method of using two orifice plates in series to determine steam quality. However, such methods actually provide only an indirect determination of steam quality because they are not directly measuring the mass and/or density of the liquid stream. They are in many cases only accurate over a limited range of conditions.

U.S. Pat. Nos. 4,689,979 and 4,773,257 to Aslesen et al., also assigned to the assignee of the present invention and incorporated herein by reference for all purposes, discloses a method of measuring the relative amounts of oil and water in a liquid stream. However, no method of determining steam quality is shown or suggested.

A "Q-Bar" device has also been described as being useful in the measurement of two phase streams. For example, the "Steamcheck Energy Monitor" sold by Baker Packers uses the "spike" resonant frequency of a resonating tube to determine steam quality. This device uses only a sample of the steam and has found to have only limited accuracy.

It is desirable, therefore, to devise an improved method of measuring wet steam.

BRIEF SUMMARY OF THE INVENTION

A method of determining total mass flow rate and phase distribution of the individual component in a flowing gas/liquid stream is disclosed. The method comprises the steps of flowing at least a first gas/liquid stream through a Coriolis-based flow meter, the first gas/liquid stream having a first known total mass flow rate and individual component phase distribution;

obtaining a first apparent total mass flow rate output and a first apparent density output from the Coriolis-based mass flow meter;

correlating the first known total mass flow rate and phase distribution with the apparent mass flow rate output and the apparent density output obtained from the Coriolis-based mass flow meter to determine a set of correlation equations;

flowing a second gas/liquid stream through the Coriolis-based mass flow meter;

obtaining a second apparent mass flow rate output and a second apparent density output from the Coriolis-based mass flow meter; and calculating the total mass flow rate and phase distribution of the second gas/liquid stream based on the aforementioned correlation equations.

Knowing total mass flow rate and phase distribution of the gas/liquid stream, the individual amounts of gas and liquid phases can also be determined arithmetically, if desired.

The generalized form of the correlation equations can be expressed as:

$$W_{app} = f(W_t; y) \quad (1)$$

and $$D_{app} = g(W_t; y) \quad (2)$$

where $W_{app}$ and $D_{app}$ are apparent mass flow rate output and apparent density output obtained from the Coriolis-based mass flow meter. $W_t$ and $y$ denote the true total mass flow rate and true phase distribution parameter of the gas/liquid flow stream.

In the step of calculating, the use of the above simultaneous correlation equations provides a means to compute two unknown variables, $W_t$ and $y$, based on the two known outputs, $W_{app}$ and $D_{app}$ obtained from the Coriolis-based mass flow meter.

Note that the term "phase distribution parameter" or the symbol "y" as used herein can be uniquely characterized by a variety of engineering parameters; such as homogeneous mixture density ($\rho_m$), no-slip liquid holdup ($\lambda$) and homogeneous vapor mass fraction (X). The adjectives, "homogeneous" and "no-slip", as used herein refer to a physical state in which the gas-liquid flow stream is perfectly mixed and both phases are flowing at the same velocity in the flow line.

These three parameters are inter-related; knowing one of the parameters, the other parameters can be determined. In wet steam measurement application, the parameter "X" is commonly referred to as "steam quality".

BRIEF SUMMARY OF THE DRAWINGS

FIG. 1 illustrates the Coriolis-based flow meter.

FIG. 2 illustrates the experimental equipment used to test the utility of the device.

FIG. 3 is a graph comparing actual quality with calculated quality using the invention described herein.

FIG. 4 is a graph comparing actual total mass flow rate with calculated total mass flow rate using the invention described herein.

DETAILED DESCRIPTION OF THE INVENTION

In the discussion herein, two-phase steam is used by way of example, but it is clear that the method could be applied to other gas/liquid streams such as natural gas/natural gas liquid streams. Referring to FIG. 1, the Coriolis-type mass flow meter of the present invention measures a very small force generated by steam fluid as it moves through a U-shaped sensor tube (1). This force results from the acceleration or deceleration of the fluid particles as the tube vibrates perpendicular to the direction of flow. The force is analogous to the Coriolis force which causes air currents to circulate around the rotating earth, and to gyroscopic forces employed in navigation systems of ships and aircraft.

The forces induced by fluid flow on the sensor tube are the Coriolis or gyroscopic-type forces. FIG. 1 shows a tube with a fluid with mass (m) and velocity (V) moving through the tube which is rotating with angular velocity ($\omega$) about axis 0—0.

The magnitude of the flow-induced Coriolis force is described by the following equation:

$$\bar{F} = 2m\bar{\omega} X \bar{V} \quad (3)$$

where $\bar{F}$ is force and $\bar{F}$, $\bar{\omega}$ and $\bar{V}$ are directional quantities and X is the vector cross product operator.

The angular velocity ($\omega$) of the sensor tube is not required to be constant, but can oscillate with a peak angular velocity ($\bar{\omega}_p$). The associated force is also oscillatory, with a peak value ($F_p$), proportional to the fluid mass (m) and velocity ($\bar{V}$).

Forces exerted by the fluid on each leg ($F_1$ and $F_2$) are opposite in direction (180 degrees out of phase). As the tube vibrates about axis 0—0, the forces create an oscillating moment ($\Delta M$) about axis R—R which is expressed by:

$$\Delta M = F_1 r_1 + F_2 r_2 \quad (4)$$

Since $F_1 = F_2$ and $r_1 = r_2$, from equations 1 and 2:

$$\Delta M = 2Fr = 4mV\omega r \quad (5)$$

Now, m (unit mass/unit length) multiplied by V (unit length/unit time) yields $\Delta Q$ (unit mass/unit time), i.e., the mass flow rate. Equation 3 then becomes:

$$\Delta M = 4\omega r \Delta Q \quad (6)$$

The total moment (M) about axis R—R due to all of the fluid particles is found by integrating Equation 4 around the sensor tube.

$$M = \int \Delta M = 4\omega r Q L \quad (7)$$

The moment M causes an angular deflection or twist of the sensor about axis R—R, which is at its maximum at the midpoint of vibrating tube travel. There is no twist at the upper and lower limits of travel since at these points $\omega$ is zero. The deflection of $\theta$ due to M is resisted by the spring stiffness ($K_s$) of the sensor tube. In general, for any torsional spring, the torque (T) is defined by:

$$T = K_s \theta \quad (8)$$

Since T=M, the mass flow rate (Q) can now be related to the deflection angle $\theta$ by combining Equations 5 and 6.

$$Q = \frac{K_s}{4\omega r L} \theta \quad (9)$$

The mass flow rate can be derived by measuring the deflection angle ($\theta$) using the sensors 2 and 3 shown in FIG. 1. This measurement is accomplished by measuring the relative times that each sensor detects the midpoint crossing of the respective leg. The time difference at zero flow is nulled. As flow increases, causing an increase in $\theta$, the time difference ($\Delta t$) between signals also increases. The velocity of the tube at the midpoint of travel ($V_t$), multiplied by $\Delta t$, is geometrically related to $\theta$ by:

$$\sin \theta = \frac{V_t}{2r} \Delta t \quad (10)$$

If $\theta$ is small, $\sin \theta$ is nearly equal to $\theta$. Also for small rotation angles, $V_t$ is the product of $\omega$ and the tube length (L), so:

$$\theta = \frac{L\omega \Delta t}{2r} \quad (11)$$

Combining equations 7 and 9 gives:

$$Q = \frac{K_s L \omega}{8r^2 \omega L} \Delta t = \frac{K_s}{8r^2} \Delta t \quad (12)$$

The mass flow rate Q is therefore proportional only to the time interval and geometric constants. Note that Q is independent of $\omega$, and therefore independent of the vibration frequency of the sensor tube.

The vibrating U-tube method of measurement also produces an output which is proportional to the density of the fluid in the meter. The output is a square wave at the natural frequency of the vibrating system. The natural frequency (f) of a spring system can be calculated directly from the mass (m) and a spring constant (k):

$$f = k \sqrt{\frac{1}{m}} \quad (13)$$

In the case of the flow tube, the vibrating system can be divided into the tube mass ($m_t$) and fluid mass ($m_f = \rho V$). The fluid mass is in turn proportional to the fluid density (p) since the tube volume is constant. Therefore, the density can be expressed directly in terms of the tube frequency (f) and constants $K_1$ and $K_2$:

$$\omega = 2\pi f = \sqrt{\frac{K}{m_t + \rho V}} \quad (14)$$

$$4\pi^2 f^2 = \frac{K}{m_t + \rho V} \quad (15)$$

$$\rho = \frac{1}{V} \left( \frac{K}{f^2 4\pi^2} - m_t \right) \quad (16)$$

let $\frac{K}{4\pi^2 V} = K_1$ and $\frac{m_t}{V} = K_2$ $$\text{giving } \rho = \frac{K_1}{f^2} - K_2 \quad (17)$$

Constants $K_1$ and $K_2$ can be determined by filling the sensor tube with two fluids of known densities (at the same temperature) and noting the resulting frequencies.

When a Coriolis-based mass flow meter is used to measure a liquid mixture stream containing two or more different types of liquids, the two fundamental outputs provided from the mass flow meter still represent the true values of the mass flow rate and the density of the liquid mixture stream being measured. U.S. Pat. No. 4,689,979 and 4,773,257 to Aslesen, et al., have disclosed a method of using the above-mentioned flow meter to determine individual amounts of two-phase liquid/liquid streams. In this particular situation, the phase distribution can be computed directly from the true density output as provided from the mass flow meter.

However, when the Coriolis-based mass flow meter is used to measure a gas/liquid two-phase flow stream, the flow meter behaves substantially differently. Although the Coriolis-based mass flow meter still provides two fundamental outputs, neither of them give true mass flow rate and true density of the gas/liquid flow as it does in a liquid/liquid mixture flow. It has been found that these two fundamental outputs, one is herein referred to as apparent mass flow rate output and the other as apparent density output, are simultaneously dependent upon both the true total mass flow rate and the true density of the gas/liquid flow stream. It has also been found that, for a given gas-liquid system, there exists an unique relationship between the true values and the apparent outputs indicated by the Coriolis-based mass flow meter.

The generalized form of the correlation equations are shown in Equations (1) and (2). The choice of the specific form of correlation equations is virtually unlimited. For example, the following simultaneous correlation equations can be used:

$$W_{app} = a_1 W_t^{a2} \rho_m^{a3} \quad (18)$$

and $$D_{app} = a_4 W_t^{a5} \rho_m^{a6} \quad (19)$$

where:
  $W_{app}$ is the apparent mass flow rate output from the Coriolis-based mass flow meter.
  $D_{app}$ is the apparent density output from the Coriolis-based mass flow meter.
  $W_t$ is the true total mass flow rate of the gas/liquid flow stream, and is equal to $W_V + W_L$.
  $W_v$ is the true mass flow rate of vapor phase.
  $W_L$ is the true mass flow rate of liquid phase.
  $\rho_m$ is the homogeneous density of the gas/liquid flow.
  $a_1$ through $a_6$ are correlation constants.

Note that an alternative form of correlation equations can also be used by replacing the parameter $\rho_m$ in the Equations (18) and (19) with either $\lambda$ or $X$, where:
  $\lambda$ is the no-slip liquid holdup.
  $X$ is the homogeneous vapor mass fraction of the vapor phase; it is defined as $W_v/W_t$, a ratio of true vapor mass flow rate to the true total mass flow rate.

Any of these parameters sufficiently quantify the gas-liquid phase distribution in the gas/liquid flows. They are also inter-related; knowing one parameter, the other two parameters can then be computed. Some identity relationships of these parameters are shown below.

$$\rho_m = \rho_L^* \lambda + \rho_v^* (1-\lambda) \quad (20)$$

$$\rho_m = 1/[X/\rho_v + (1-X)/\rho_L] \quad (21)$$

$\rho_v$ and $\rho_L$ are, respectively, the known densities of pure vapor phase and pure liquid phase under the operating condition.

Another form of simultaneous correlation equations can also take the form of:

$$W_{app} = b_1 W_t^{b2} \rho_m^{b3} \quad (22)$$

and $$D_{app} = b_4 W_v^{b5} \rho_m^{b6} \quad (23)$$

where $b_1$ through $b_6$ are correlation constants. Equations (22) and (23) still conform the generalized form set forth by Equations (1) and (2), although $W_v$ is used here in Equation (23) instead of $W_t$. This is because that $W_v$ is a function of $W_t$ and $X$ (i.e., $W_v = W_t * X$), and $X$ is a function of $\rho_m$ (Equation (21)), it therefore follows that $D_{app}$ is a function of $W_t$ and $\rho_m$ as defined in Equation (1).

Similarly, still another example of correlation equations can be expressed as:

$$W_{app} = c_1 W_t^{c2} \lambda^{c3} \quad (24)$$

and $$D_{app} = c_4 W_t^{c5} \lambda^{c6} \quad (25)$$

where $c_1$ through $c_6$ are correlation constants.

EXAMPLE

To test the utility of the above-described invention, the experimental apparatus illustrated in FIG. 2 was used. Air and water were used to test the two-phase flow measurement abilities of a Coriolis-based mass flow meter 3.

In particular, a Model D-150 mass flow meter manufactured by Micro Motion, Inc. was used in the test.

Compressed air flowed into the system via compressed air line 4 and water flowed into the system via a tank 5 and water line 6 through a pump 7. The flow rates of air and water were monitored with meters 8 and 9 respectively. The flow rates of air and water were regulated with valves 10 and 11 respectively. After mixing, air and water were thoroughly agitated and dispersed in static mixer 12.

Flow tests were run at high air-water ratios to simulate steam flow conditions. At this range of air-water rates, the flow is homogeneous with water droplets being entrained by the air stream.

During each test run, air flow rate was kept constant and water flow rate was allowed to vary. Tests at the same air flow rate were then repeated at different line pressures.

Experiments were run for air rates ranging from 100 to 167 standard cu. ft. per minute, water rates ranging from 0.5 to 2.6 gallons per minute and line pressures ranging from 20 to 120 pounds per square inch absolute.

A data acquisition system 13 was used to record flow data comprising air and water flow rates, line static pressure and the apparent mass flow rate output and the apparent density output from the Coriolis-based mass flow meter.

Equations (22) and (23) were used to correlate the test data. A multi-variable least square analysis is utilized to determine the correlation constants $b_1$ through $b_6$, yielding the following simultaneous correlation equations:

$$W_{app} = 0.7186 \; W_t^{1.0511} \rho_m^{0.2274} \quad (26)$$

$$D_{app} = 11.1465 \ W_v^{-0.2805} \rho_m^{0.0647} \quad (27)$$

where $W_t$ is the true total mass flow rate of air and water, $W_v$ is the true air mass flow rate, $\rho_m$ is the homogeneous mixture density of air/water, and $W_{app}$ and $D_{app}$ are, respectively, the apparent density and the apparent mass flow rate output from the Micro Motion mass flow meter.

To verify the validity of the correlation equations, the calculated air quality (X calc) and the actual air quality (X meas) for all test data are compared in FIG. 3. Also, the calculated total mass flow rate ($W_t$ calc) and the actual mass flow rate ($W_t$ meas) are compared in FIG. 4. FIG. 3 is constructed by generating the calculated and measured $\rho_m$ values, then using the relationship in Equation (21) to compute the corresponding X values.

This example illustrates the utility of the present invention.

It is to be understood that the above embodiments are intended to be illustrative and not restrictive. Most notably, the invention could be used to measure the relative amounts of liquid and vapor in flow streams other than air/water mixture and wet steam. The scope of the invention, therefore, should be interpreted not with reference to the above description, but with reference to the appended claims, along with the full range of equivalents thereto.

What is claimed is:

1. A method of determining total mass flow rate and phase distribution of individual components in a flowing gas/liquid stream comprising the steps of:
    flowing at least a first gas/liquid stream through a Coriolis-based flow meter, the first gas/liquid stream having a first known total mass flow rate and component phase distribution;
    obtaining a first apparent total mass flow rate output and a first apparent density output from the Coriolis-based mass flow meter;
    correlating the first known total mass flow rate and phase distribution with the first apparent mass flow rate output and the first apparent density output obtained from the Coriolis-based mass flow meter to determine a set of correlation equations;
    flowing a second gas/liquid stream through the Coriolis-based mass flow meter;
    obtaining a second apparent mass flow rate output and a second apparent density output from the Coriolis-based mass flow meter;
    calculating a total mass flow rate and a component phase distribution of the second gas/liquid stream based on the correlation equations and the second apparent mass flow rate output and the second apparent density output.

2. The method as recited in claim 1 wherein the step of correlating uses two simultaneous correlation equations to relate the first apparent mass flow rate output and the first apparent density output obtained from the Coriolis-based mass flow meter with a true mass flow rate and a component phase distribution parameter of the gas/liquid two-phase flow of the form:

$$W_{app} = f(W_t; y)$$

and $$D_{app} = g(W_t; y)$$

wherein $W_{app}$ is the first apparent mass flow rate output obtained from the Coriolis-based mass flow meter, $D_{app}$ is the first apparent density output obtained from the Coriolis-based mass flow meter, $W_t$ is the true total mass flow rate of the gas/liquid flow stream, and y is the component phase distribution parameter of the gas/liquid flow stream.

3. The method as recited in claim 2 wherein the correlation equations are of the form:

$$W_{app} = a_1 \ W_t^{a_2} \rho_m^{a_3}$$

and $$D_{app} = a_4 \ W_t^{a_5} \rho_m^{a_6}$$

wherein $a_1$, $a_2$, $a_3$, $a_4$, $a_5$, and $a_6$ are correlation constants, and $P_m$ is homogeneous density of the gas/liquid mixture.

4. The method as recited in claim 3 wherein the homogeneous density of the gas/liquid mixture parameter, $\rho_m$, in both correlation equations is substituted with a parameter "$\lambda$", the no-slip liquid holdup.

5. The method as recited in claim 3 wherein the homogeneous density of the gas/liquid, mixture parameter, $\rho_m$, in both correlation equations is substituted with a parameter "X", the homogeneous mass fraction of the vapor phase.

6. The method as recited in claim 1 wherein said gas/liquid stream includes two-phase streams of varying composition.

7. The method of claim 1, further comprising the step of:
    determining the relative amount of gas and liquid in the second gas/liquid stream from the total mass flow rate and the second component phase distribution.

* * * * *